(12) United States Patent
Segnalini et al.

(10) Patent No.: US 8,703,955 B2
(45) Date of Patent: Apr. 22, 2014

(54) PROCESS FOR THE RESOLUTION OF ISOQUINOLINE DERIVATIVES

(75) Inventors: Franca Segnalini, Borgo Grappa (IT); Angela Tuozzi, Rome (IT); Angelo Gentile, Cernusco sul Naviglio (IT)

(73) Assignee: Recordati Industria Chimica e Farmaceutica S.p.A., Milan (IT)

( * ) Notice: Subject to any disclaimer, the term of this patent is extended or adjusted under 35 U.S.C. 154(b) by 196 days.

(21) Appl. No.: 12/808,255

(22) PCT Filed: Feb. 25, 2009

(86) PCT No.: PCT/EP2009/052234
§ 371 (c)(1),
(2), (4) Date: Jun. 15, 2010

(87) PCT Pub. No.: WO2009/106547
PCT Pub. Date: Sep. 3, 2009

(65) Prior Publication Data
US 2010/0298570 A1 Nov. 25, 2010

(30) Foreign Application Priority Data
Feb. 28, 2008 (IT) .............. MI2008A0319

(51) Int. Cl.
*C07D 217/00* (2006.01)
*A61K 31/47* (2006.01)

(52) U.S. Cl.
USPC .......................................... 546/147; 514/307

(58) Field of Classification Search
None
See application file for complete search history.

(56) References Cited

U.S. PATENT DOCUMENTS 6,015,903 A * 1/2000 Viergutz et al. ............... 546/147
6,670,476 B2 * 12/2003 Harms ........................ 544/349

FOREIGN PATENT DOCUMENTS

EP 0181055 A 5/1986
WO 2006/013581 A 2/2006

OTHER PUBLICATIONS

Kozma, D., ed., "Optical Resolutions Via Diastereomeric Salt Formation," 2002, CRC Press, p. 16.*
Pandit, N. Pharmaceutical Salts Lippincott 2007 p. 19.*

* cited by examiner

*Primary Examiner* — Heidi Reese
(74) *Attorney, Agent, or Firm* — Lucas & Mercanti, LLP

(57) ABSTRACT

A process for the resolution of racemic tetrahydropapaverine with optically active arylpropionic acids is described.

19 Claims, No Drawings

PROCESS FOR THE RESOLUTION OF ISOQUINOLINE DERIVATIVES

CROSS-REFERENCE TO RELATED APPLICATIONS

This application is a 371 of PCT/EP2009/052234 filed on Feb. 25, 2009, which claims the benefit of Italian Patent Application No. MI2008A000319 filed on Feb. 28, 2008, the contents of each of which are incorporated herein by reference.

FIELD OF THE INVENTION

The present invention relates to a new process for the resolution of racemic tetrahydropapaverine (I), more particularly to a process for the resolution of racemic tetrahydropapaverine (I) with optically active arylpropionic acids.

STATE OF THE ART

The compound (±)-1-[(3,4-dimethoxyphenyl)methyl]-1,2,3,4-tetrahydro-6,7-dimethoxy-isoquinoline, commonly known as tetrahydropapaverine or (R,S)-THP, of formula

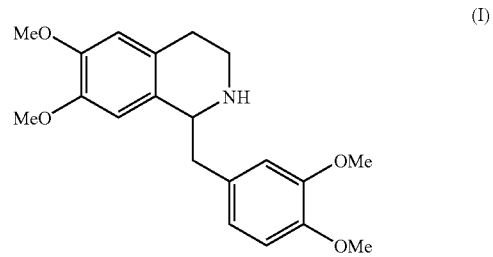 [SMILES: COc1ccc(CC2NCCc3cc(OC)c(OC)cc32)cc1OC]

is an intermediate useful for the synthesis of pharmaceutical compounds, including for example atracurium besylate of formula

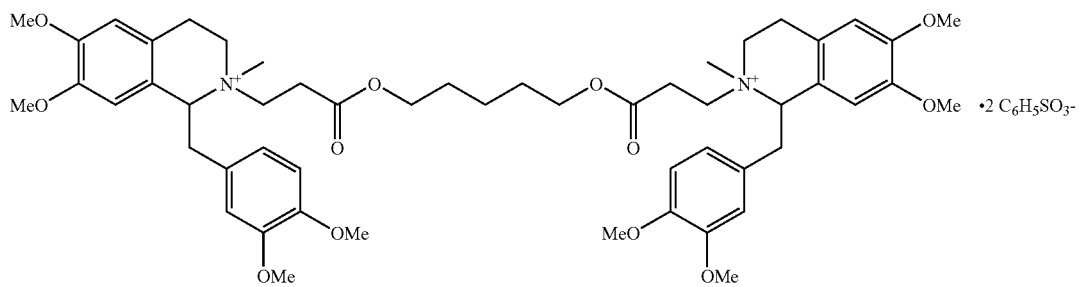 [SMILES: COc1ccc(CC2c3cc(OC)c(OC)cc3CC[N+]2(C)CCC(=O)OCCCCCOC(=O)CC[N+]2(C)CCc3cc(OC)c(OC)cc3C2Cc2ccc(OC)c(OC)c2)cc1OC ; "·2 C6H5SO3-"]

a known muscle-relaxant, used in general anesthesia and in severe myasthenia. Atracurium is sold as a mixture and, preferably, as the most potent single isomer 1R,1'R,2R,2R', known as cis-atracurium of formula

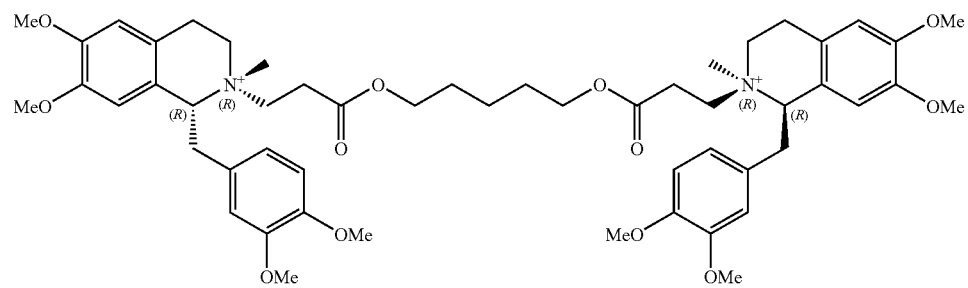

Cis-atracurium can be prepared by isolation from mixtures of atracurium cis and trans 1R,1R' isomers, in their turn obtained by reaction of (R)-tetrahydropapaverine or (R)-THP, of formula

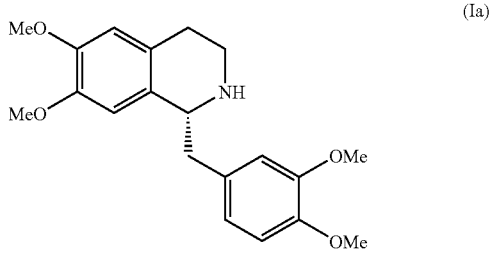 [SMILES: COc1ccc(C[C@H]2NCCc3cc(OC)c(OC)cc32)cc1OC]

with 1,5-pentamethylene diacrylate, as described, for example, in U.S. Pat. No. 5,453,510 (Burroughs Wellcome).

Several processes for the preparation of (R)-THP (Ia) are known in the literature, and among them, in particular, some methods based on the resolution of (R,S)-THP (I) by reaction with optically active acids, subsequent separation of the resultant diastereisomeric compounds and final obtainment of (R)- or (S)-THP (Ia or Ib).

For example, CN101037411 (Nanjing University) describes a rather complicated method for the resolution of (R,S)-THP (I) consisting in precipitating the isomer (S)-THP (Ib) as compound with L-amino acids and in treating the mother liquors enriched in (R)-THP (Ia) to subsequent resolution with different resolving agents, such as alpha-phenoxypropionic acids or D-amino acids. CN1634892 (Xuzhou Nhwa Pharm.) discloses the preparation of (R)-THP (Ia) by resolution of the racemic mixture with N-acyl-D-amino acids (non-natural), that is with expensive and not easy available agents.

The paper published on J. Chem. Soc. Trans. (1898), 73, 902-905 discloses the resolution of THP (I) with (+)-alpha-bromocanphorsulphonic acid, an agent with poor industrial applicability because it is little stable, irritant and very expensive, and further discloses a failed attempt to resolve with tartaric acid.

U.S. Pat. No. 5,453,510 (Burroughs Wellcome) describes the resolution of (R,S)-THP (I) by salification with N-acetyl-L-leucine: in this case the desired isomer (R)-THP (Ia) remains in solution, so requiring subsequent cumbersome steps for its recovery.

U.S. Pat. No. 6,015,903 (BASF) describes the use of (+) or (−) 2-(2,4-dichlorophenoxy)-propionic acid as resolving agent for (R,S)-THP (I), with the obtainment of (+)-THP, corresponding to (R)-THP (Ia), with an enantiomeric excess (e.e.) from about 90 to about 99%. However, the method does not appear particularly attractive for the preparation of intermediates for pharmaceutical use, since the resolving agent is a herbicide, potentially toxic in the process as well as in the finished product, even if present only in traces.

EP181055 (Wellcome) describes the resolution of 5'-methoxylaudanosine with (+)-dibenzoyl tartaric acid while EP866394 (Knorr-Bremse) discloses a similar separation of diastereoisomers of tetrahydrodibenzoisoquinolines with D-toluoyltartaric acid: both methods use a substrate different from (R,S)-THP (I) and resolving agents with a non-natural configuration, difficult to prepare and expensive to purchase.

WO2007/091753 (Chong Kun Dang Pharm.) discloses the resolution of (R,S)-THP (I) with (S)- or (R)-phenylglycine, with good enantiomeric excess but obtained by cooling to low temperatures (−20/−30° C.) in the crystallization step.

The methods described in the literature generally use equimolar amounts of resolving agents. We have now surprisingly found a process for the resolution of (R,S)-THP (I) particularly simple and advantageous from the industrial point of view, which allows to obtain (R)-THP (Ia) at room temperature, with high e.e. and very good yields, by using cheap and readily available resolving agents, particularly suitable for the use in pharmaceutical field, in amount lower than those reported in the literature.

GENERAL DESCRIPTION OF THE INVENTION

Therefore, object of the present invention is a process for the resolution of (R,S)-THP (I) with an optically active arylpropionic acid, optionally in admixture with a further optically active acid or with an inorganic acid, in a suitable solvent system.

DETAILED DESCRIPTION OF THE INVENTION

The process object of the present invention allows the resolution of (R,S)-THP (I) using an optically active arylpropionic acid as resolving agent in a suitable solvent system.

The optically active arylpropionic acid can be used alone or in admixture with a further optically active acid or with an inorganic acid.

The resolution process object of the present invention comprises the following steps:
a) contacting (R,S)-THP (I) with the optically active arylpropionic acid, optionally in admixture with a further optically active acid or with an inorganic acid, in a suitable solvent system,
b) separating the diastereoisomeric compound of (R)-THP precipitated from the mixture,
c) recovering (R)-THP (Ia) from the separated diastereoisomer, and/or optionally
d) recovering (S)-THP (Ib) from the mother liquor.

In the present context, the term arylpropionic acid means a propionic acid derivative bearing in position α or β an optionally substituted phenyl or naphthyl group.

Specific examples of optically active arylpropionic acids suitable as resolving agents in the process object of the present invention are pharmaceutically acceptable arylpropionic acid such as (S)-naproxen, (S)-ibuprofen, (S)-flurbiprofen, and (S)-tropic acid.

The preferred optically active arylpropionic acid is (S)-naproxen or (+)-(S)-2-(6-methoxynaphthalen-2-yl)propionic acid, a known anti-inflammatory drug (Merck Index no. 6504, ed. 1996) of formula

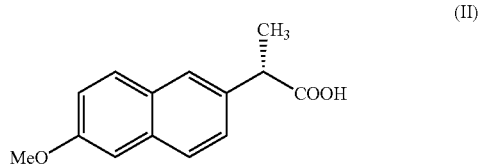 [SMILES: COc1ccc2cc([C@H](C)C(=O)O)ccc2c1]

herein after referred to as (S)-naproxen (II).

Specific examples of optically active acids which can be optionally used together with the optically active arylpropionic acid in the resolution process of the invention are (R)-mandelic acid, (S)-O-acetylmandelic acid, L-phenyl lactic acid, (R)- and (S)-methoxyphenylacetic acid, (S)-phenylpropionic acid, (R)- and (S)-tropic acid; (R)-mandelic acid being preferred. When the resolving acid is used in admixture with an inorganic acid, preferred inorganic acids are aqueous hydrogen halides, sulphuric acid and phosphoric acid, hydrochloric acid being particularly preferred.

In step a) of the present process (R,S)-THP and the resolving agent are put in contact in solution in a suitable solvent system and at suitable concentrations.

(R,S)-THP (I) can be directly used as free base or can be previously liberated from a salt thereof, such as for example THP (I) hydrochloride, according to known procedures.

In a similar way, the optically active arylpropionic acid as well as the optional optically active acid can be directly used as free acids or can be previously liberated from their salts, most commonly from their respective sodium salts, according to known procedures.

Starting (R,S)-THP (I) can be a racemic mixture, wherein the enantiomeric ratio (R):(S) is about 1:1, or a mixture wherein the two enantiomers are not present in equimolar amounts, preferably a mixture enriched in the (R) isomer in case the preparation of (R)-THP (Ia) with a high enantiomeric excess is desired.

The solvent system is generally selected among ketones, lower alcohols, aromatic hydrocarbons and mixtures thereof, optionally in the presence of water.

Specific examples of solvents used in the resolution process object of the present invention are acetone, methylethylketone (MEK), methylisobutylketone (MIBK), methanol, ethanol, isopropanol (IPA) and toluene. The preferred solvents are acetone and ethanol.

When water is present in the solvent system, the amount is generally lower than 20% (v/v). The solvent is generally used in a volume/weight ratio with respect to the starting (R,S)-THP (I) from 2:1 to 15:1, preferably about 15:1.

In the present process the optically active arylpropionic acid is generally used in a ratio of equivalents from 0.3:1 to 1:1 with respect to (R,S)-THP (I), preferably from 0.35:1 to 0.8:1, more preferably from 0.40:1 to 0.65:1.

When a further optically active acid or an inorganic acid is used in addition to the optically active arylpropionic acid, the overall ratio of equivalents is generally 1:1, and the ratio of the equivalents of the optically active arylpropionic acid and the further acid is generally from 8:2 to 1:1, preferably 7:3.

The temperature is not a critical parameter in the resolution process object of the present invention which can be carried out at temperatures generally ranging from 0° C. to 80° C. However, it is important to underline that the preferred process temperature is from 20° C. to 30° C., still more preferably around 25° C.

According to a preferred embodiment of the present invention, (R,S)-THP (I) is resolved by using (S)-naproxen (II) as resolving agent, optionally in admixture with hydrochloric acid. Therefore, a further object of the present invention is a resolution process comprising the following steps:

a') contacting (R,S)-THP (I) with (S)-naproxen (II), optionally in admixture with a further optically active acid or with an inorganic acid, in a suitable solvent system, b') separating the diastereoisomeric compound (R)-THP.(S)-naproxen (IIIa) precipitated from the mixture, c') recovering (R)-THP (Ia) from the separated diastereoisomer (IIIa), and/or optionally d') recovering (S)-THP (Ib) from the mother liquor.

The process for the resolution of (R,S)-THP with (S)-naproxen is depicted in the following scheme:

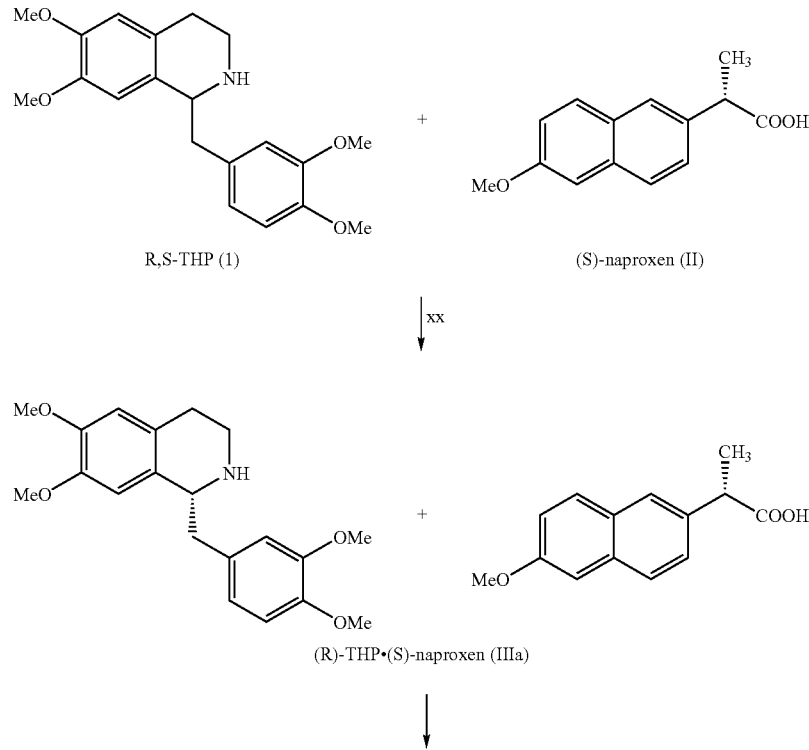

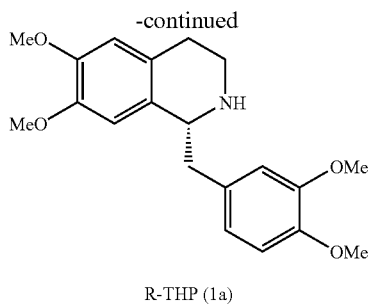

R-THP (1a)

After contacting (R,S)-THP (I) and (S)-naproxen (II) in solution in the suitable solvent system, a mixture (III) of the diastereoisomeric compounds (R)-THP.(S)-naproxen (IIIa) and (S)-THP.(S)-naproxen (IIIb) forms, generally followed by precipitation of the compound (R)-THP.(S)-naproxen (IIIa) and, consequently, by the enrichment of the mother liquor in the compound (S)-THP.(S)-naproxen (IIIb) and in (S)-THP enantiomer (Ib).

The compounds (R)-THP.(S)-naproxen (IIIa) and (S)-THP.(S)-naproxen (IIIb) are a further object of the present invention.

When (R)-THP (Ia) is desired, the present process is particularly advantageous with respect to some resolution methods described in the literature, since it is characterized by the direct precipitation of compound (R)-THP.(S)-naproxen (IIIa) comprising the desired isomer, with remarkable simplification of the subsequent recovery steps and yield increase.

The precipitated diastereoisomeric compound (R)-THP.(S)-naproxen (IIIa) is then separated from the mixture, preferably by filtration, and used, after optional drying, for the recovery of (R)-THP (Ia) or for a further purification through one or more crystallizations of the compound itself, preferably from acetone or from ethanol.

The subsequent step c') of the present process consists in recovering (R)-THP (Ia) from the separated and optionally crystallized compound (R)-THP.(S)-naproxen (IIIa), according to procedures known to the skilled in the art, generally by treatment of compound (IIIa) with bases, in a suitable water/immiscible organic solvent biphasic system, then isolating (R)-THP (Ia) from the organic phase, generally by evaporation.

The process object of the present invention, even if particularly advantageous for obtaining (R)-THP (Ia) with high enentiomeric excess and weight yield, can be also used for isolating (S)-THP (Ib) from the mother liquor. For example, after evaporation from the mother liquor, the residue is taken up with toluene and added with a sodium hydroxide aqueous solution (1-2 equivalents with respect to THP). After separation of the phases, the organic phase is washed with water, to remove the residual basicity and concentrated to residue, giving a residue enriched in (S)-THP (Ib).

According to a further preferred embodiment, (R)-THP (Ia) or optionally (S)-THP (Ib), prepared according to the process object of the present invention, are subsequently salified, preferably as hydrochlorides, according to procedures known to the skilled in the art, to give crystalline compounds with improved handiness and preservability.

In a particularly preferred embodiment, (R,S)-THP (I) is dissolved at room temperature in 10 volumes of acetone, 0.4 equivalents of (S)-naproxen (II) are added to the solution which is kept under stirring for 10-16 hours at room temperature, filtered, washed with acetone and dried in oven at 40° C.

The compound is suspended in toluene/water (3-4 volumes, 1:1 mixture), 1.1 equivalents of NaOH are added and kept under stirring. The phases are separated, the aqueous phase is extracted with 1 volume of toluene, the organic phases are collected, washed with water and concentrated under vacuum, obtaining (R)-THP (Ia) with high enantiomeric excess.

In a further particularly preferred embodiment, (R,S)-THP (I) is dissolved at room temperature in 15 volumes of ethanol, 0.7 equivalents of (S)-naproxen (II) and 0.3 equivalents of HCl are added to the solution which is kept under stirring for 16 hours at 25-35° C., filtered, washed with 1 volume of ethanol and dried in oven at 40° C.

(R)-THP obtained according to the present process is an intermediate useful for the preparation of cis-atracurium. A further object of the present invention is a process for the preparation of cis-atracurium comprising the preparation of (R)-THP by resolution with an optically active arylpropionic acid, optionally in admixture with a further optically active acid or with an inorganic acid.

The process object of the present invention is now illustrated by some examples, herein reported without any limiting purpouse.

EXAMPLES

Analysis:
(R)- and (S)-THP determination: HPLC column chiracel OD 4.6×250 mm; eluent: hexane/isopropanol 85/15; flow: 1.5 ml/min; UV detector λ:231 nm, T: 25° C.

Example 1

Preparation of (R,S)-THP (I) Free Base from (R,S)-THP Hydrochloride

Racemic (R,S)-THP HCl (53 g, preparable for example as described in Arch. Pharm. 1934, 272, 236-41) was put in contact with toluene (2-4 volumes), water (3-5 volumes), aqueous 30% NaOH (2 equivalents) and kept under stirring at room temperature for 15 minutes. The phases were separated and the aqueous phase was extracted with toluene (1-1.5 volumes).

The collected organic phases were washed twice with water and concentrated under vacuum at 70° C. up to residue. (R,S)-THP (I) was obtained as an oil (50 g).

Example 2

Formation of the Compound of (R,S)-THP (I) with (S)-Naproxen (II)

(R,S)-THP base (50 g), prepared as described in example 1, was dissolved in acetone (10 volumes) at room temperature.

(S)-naproxen (II) (13.4 g; 0.4 eq.), commercially available or preparable for example according to U.S. Pat. No. 4,009,197, was added and the precipitation of a crystalline solid was observed. The suspension was kept under stirring for 10-16 hours at room temperature, filtered, washed with acetone (1 volume) and dried in oven at 40° C. Compound (R)-THP.(S)-naproxen (IIIa) (30 g; e.e.: 96.2%) was obtained.

Example 3

Purification of Compound (R)-THP.(S)-Naproxen (IIIa)

Compound (R)-THP.(S)-naproxen (IIIa) (30 g), prepared as described in example 2, was dissolved in acetone (6 volumes) under reflux. After 1 hour under stirring and under reflux, the mixture was cooled at room temperature. The precipitate was filtered on Buckner, washed with acetone (1 volume) and dried in oven at 40° C. Compound (R)-THP.(S)-naproxen (IIIa) (24 g; e.e.: 98.8%) was obtained.

$^1$H-NMR (200 MHz, DMSO) ppm: 7.8-6.8 (m, 11H); 3.8-3.4 (2 s, 15H); 3.2-3.0 (m, 4H); 2.8-2.6 (m, 2H); 2.6-2.5 (m, 2H); 1.4 (d, 3H).

Example 4

Recovery of (R)-THP (Ia) from Compound (R)-THP.(S)-Naproxen (IIIa)

Compound (R)-THP.(S)-naproxen (IIIa) (14 g), prepared as described in example 3, was put into contact with toluene (3-4 volumes), water (3-4 volumes) and aqueous 30% NaOH (1.1 eq) at room temperature and kept under stirring for 15 minutes. The phases were separated and the aqueous phase was extracted with toluene (1 volume). The collected organic phases were washed twice and concentrated under vacuum to residue. (R)-THP (Ia) (8.6 g; e.e.: 99.8%) as an oil was obtained.

Example 5

Preparation of (R)-THP Hydrochloride

Absolute EtOH (6 volumes) was added to a residue of (R)-THP (Ia) (8.6 g), prepared as described in example 4. Aqueous 37% HCl (2.48 g; 1.05 eq) was added at room temperature to the resultant solution. At the end of the addition, the solution was kept under stirring and after 10 minutes the precipitation of the compound started. After 1 hour at room temperature, the precipitate was filtered on buckner, washed with EtOH (1 volume) and dried in oven under vacuum at 70° C.

(R)-THP HCl (7 g; e.e.: 99.8%) was obtained.

Examples 6-9

Preparation of (R)-THP (Ia) by Resolution of (R,S)-THP (I) with (S)-Naproxen (II)

Following substantially the same procedures described in examples 1-4, the following experiments for the preparation of (R)-THP (Ia) by resolution of (R,S)-THP (I) with (S)-naproxen (II) were carried out, obtaining the results reported in table 1.

Example 10

Recrystallization of Compound (R)-THP.(S)-Naproxen (IIIa)

A sample of compound (R)-THP.(S)-naproxen (IIIa), prepared as described in example 6 and with an e.e. =40%, was recrystallized according to the conditions and with the results reported in table 1.

TABLE 1

| Ex. | Starting racemic THP (I) (g) | Naproxen (eq.) | Solvent/ vol. vs weight racemic THP (I) | compound III (g) | e.e. (%) | Yield % mol vs (R)-THP |
|---|---|---|---|---|---|---|
| 6 | 5 | 0.65 | Acetone/8 | 4.5 | 40 | 69 |
| 7 | 5 | 0.45 | Acetone/10 | 3.4 | 70 | 69 |
| 8 | 50 | 0.40 | Acetone/10 | 30 | 96 | 70 |
| 9 | 20 60% ee | 0.45 | Acetone/10 | 15 | 98.8 | 56 |
| 10 | 4 40% ee | — | Acetone/6.0 | 3.2 | 66 | 66.4 |

Examples 11-21

Preparation of (R)-THP (Ia) by Resolution of (R,S)-THP (I) with (S)-Naproxen (II)

Following substantially the same procedures described in examples 1-4, the following experiments for the preparation of (R)-THP (Ia) by resolution of (R,S)-THP (I) with (S)-naproxen (II) were carried out, obtaining the results reported in table 2.

TABLE 2

| Ex. | Starting racemic THP (I) (g) | Naproxen (eq.) | Solvent/ vol. vs weight racemic THP (I) | T (° C.) | compound III (g) | e.e. (%) | Yield % mol vs (R)-THP |
|---|---|---|---|---|---|---|---|
| 11 | 5 | 0.65 | toluene/2.4 | 25 | 6.1 | 12 | 56 |
| 12 | 5 | 0.65 | Acetone/8 | 25 | 4.5 | 38 | 69 |
| 13 | 5 | 0.45 | Acetone/10 | 25 | 3.4 | 70 | 69 |
| 14 | 50 | 0.40 | Acetone/10 | 25 | 30 | 96 | 70 |
| 15 | 10 | 0.45 | IPA/10 | 25 | 6.5 | 83.2 | 71 |
| 16 | 17 | 0.45 | EtOH/10 | 25 | 10.5 | 89.1 | 70 |
| 17 | 10 | 0.45 | MeOH/10 | 25 | 2 | 99.6 | 24 |
| 18 | 10 | 0.45 | MeOH/5 | 25 | 4 | 99.8 | 48 |
| 19 | 10 | 0.65 | MeOH/10 | 25 | 4.6 | 99.8 | 55 |
| 20 | 50 | 0.40 | MEK/10 | 25 | 30.6 | 97.9 | 71 |
| 21 | 50 | 0.40 | MEK/10 | 70 | 30.3 | 89.1 | 68 |

Examples 22-36

Preparation of (R)-THP (Ia) by Resolution of (R,S)-THP (I) with (S)-Naproxen (II) and (R)-Mandelic Acid Following substantially the same procedures described in examples 1-4, the following experiments for the preparation of (R)-THP (Ia) by resolution of (R,S)-THP (I) with (S)- naproxen (II) in admixture with (R)-mandelic acid were carried out, obtaining the results reported in table 3.

TABLE 3

| Ex | Starting racemic THP (I) (g) | mandelic acid/ naproxen (eq.) | Solvent | vol. vs weight racemic THP (I) | T (° C.) | e.e. (%) | Yield % mol vs (R)-THP |
|---|---|---|---|---|---|---|---|
| 22 | 10 | 0.5/0.5 | acetone | 12.4 | 25 | 97.8 | 34.6 |
| 23 | 10 | 0.35/0.65 | acetone | 12.7 | 25 | 97.6 | 77.0 |
| 24 | 50 | 0.30/0.70 | acetone | 15 | 25 | 90.14 | 81 |
| 25 | 10 | 0.35/0.65 | MEK | 12.7 | 25 | 88.8 | 72.7 |
| 26 | 10 | 0.35/0.65 | EtOH | 12.7 | 25 | 97.6 | 82.1 |
| 27 | 10 | 0.30/0.70 | EtOH | 12.8 | 25 | 96.6 | 87 |
| 28 | 60 | 0.30/0.70 | EtOH | 10 | 25 | 91.6 | 87 |
| 29 | 12.6 | 0.30/0.70 | EtOH | 10 | 70 | 91.19 | 85 |
| 30 | 60 | 0.30/0.70 | EtOH | 15 | 25 | 98.46 | 86 |
| 31 | 50 | 0.30/0.70 | EtOH | 15 | 25 | 94.54 | 85 |
| 32 | 60 | 0.30/0.70 | EtOH | 10 | 25-0 | 86.22 | 85 |
| 33 | 60 | 0.30/0.70 | MeOH | 10 | 25 | 99.94 | 60 |
| 34 | 50 | 0.30/0.70 | EtOH/H$_2$O 95/5 | 5 | 25 | 99.30 | 75 |
| 35 | 50 | 0.30/0.70 | EtOH/H$_2$O 90/10 | 10 | 25 | 99.70 | 75 |
| 36 | 50 | 0.30/0.70 | EtOH | 15 | 78 | 95.40 | 82 |

Examples 37-53

Preparation of (R)-THP (Ia) by Resolution of (R,S)-THP (I) with (S)-Naproxen (II) and Hydrochloric Acid Following substantially the same procedures described in examples 1-4, the following experiments for the preparation of (R)-THP (Ia) by resolution of (R,S)-THP (I) with (S)-naproxen (II) in admixture with hydrochloric acid were carried out, obtaining the results reported in table 4.

TABLE 4

| Ex | Starting racemic THP (I) (g) | HCl/naproxen (eq.) | Solvent | vol. vs weight racemic THP (I) | T (° C.) | e.e. (%) | Yield % mol vs (R)-THP |
|---|---|---|---|---|---|---|---|
| 37 | 5 | 0.30/0.70 | Acetone | 15 | 25 | 53.10 | 76 |
| 38 | 50 | 0.30/0.70 | EtOH | 15 | 25 | 96.50 | 85 |
| 39 | 50 | 0.30/0.70 | EtOH/H$_2$O 95/5 | 5 | 25 | 54.00 | 88 |
| 40 | 50 | 0.30/0.70 | EtOH/H$_2$O 95/5 | 5 | 25 | 40.80 | 82 |
| 41 | 50 | 0.30/0.70 | EtOH/H$_2$O 95/5 | 5 | 25-0 | 6.60 | 84 |
| 42 | 35 | 0.30/0.70 | EtOH | 15 | 25 | 97.16 | 89 |
| 43 | 609 | 0.30/0.70 | EtOH | 15 | 25 | 98.78 | 88 |
| 44 | 50 | 0.30/0.70 | EtOH | 15 | 35-25 | 99.10 | 85 |
| 45 | 50 | 0.30/0.70 | EtOH | 15 | 75-60 | 99.06 | 84 |
| 46 | 50 | 0.30/0.70 | EtOH | 15 | 10 | 76.40 | 82 |
| 47 | 50 | 0.20/0.80 | EtOH | 15 | 25 | 77.45 | 85 |
| 48 | 50 | 0.40/0.60 | EtOH | 15 | 25 | 63.50 | 78 |
| 49 | 50 | 0.30/0.70 | EtOH + 30% toluene | 15 | 25 | 98.40 | 81 |
| 50 | 67.5 | 0.30/0.70 | IPA | 15 | 25-37 | 13.00 | 90 |
| 51 | 67.5 | 0.30/0.70 | IPA/H$_2$O 95/5 | 15 | 25-28 | 23.00 | 83 |
| 52 | 33.7 | 0.30/0.70 | IPA/H$_2$O 80/20 | 15 | 18-26 | 36.60 | 52 |
| 53 | 33.7 | 0.30/0.70 | IPA/H$_2$O/MeOH 80/20/5 | 15 | 25-35 | 99.62 | 49 |

Example 54

Preparation of (R)-THP (Ia) by Resolution of (R,S)-THP (I) with (S)-Ibuprofen and Hydrochloric Acid Following substantially the same procedures described in examples 1-4, (R)-THP (Ia) (e.e. 94.90%, 47% yield) was obtained by resolution of (R,S)-THP (I) with (S)-ibuprofen in admixture with hydrochloric acid (eq. ratio 0.7/0.3) in ethanol (15 volumes).

The invention claimed is:
1. A process for the resolution of (R,S)-tetrahydropapaverine (THP) (I) with an optically active arylpropionic acid, in admixture with an optically active acid or with an inorganic acid, in a suitable solvent system comprising:
    a) contacting (R,S)-THP (I) with an optically active arylpropionic acid, in admixture with an optically active acid or with said inorganic acid, in a suitable solvent system,
    b) separating the diastereoisomeric compound of (R)-THP precipitated from the mixture,
    c) recovering (R)-THP (Ia) from the separated diastereoisomer; and/or optionally
    d) recovering (S)-THP (Ib) from the mother liquor
    wherein
    the ratio of equivalents of optically active arylpropionic acid to (R,S)-THP is in the range of 0.3:1-1:1 with respect to (R,S)-THP.
2. A process according to claim 1 wherein the optically active arylpropionic acid is selected from the group consisting of (S)-naproxen, (S)-ibuprofen, (S)-flurbiprofen and (S)-tropic acid.
3. A process according to claim 2 wherein the optically active arylpropionic acid is (S)-naproxen.

4. A process 4 comprising the following steps:
a') contacting (R,S)-THP (I) and (S)-naproxen (II) in solution in a suitable solvent system,
b') separating the diastereoisomeric compound (R)-THP.(S)-naproxen (Ma) precipitated from the mixture; and
c') recovering (R)-THP (Ia) from the separated diastereoisomer (IIIa)
wherein the ratio of equivalents of (S)-naproxen (II) to (R,S)-THP (I) is in the range of 0.3:1-1:1 with respect to (R,S)-THP.

5. A process according to claim 1 wherein the inorganic acid is an aqueous hydrogen halide.

6. A process according to claim 1 wherein the solvent system is selected from the group consisting of ketones, lower alcohols, aromatic hydrocarbons and mixtures thereof, optionally in the presence of water.

7. A process according to claim 1 wherein the solvent is selected from the group consisting of acetone, methylethylketone, methylisobutylketone, methanol, ethanol, isopropanol, toluene and mixtures thereof.

8. A process according to claim 1 wherein the solvent is used in a volume/weight ratio of the starting (R,S)-THP (I) of from 2:1 to 15:1.

9. A process according to claim 1 wherein the optically active arylpropionic acid is used in a ratio of equivalents of from 0.3:1 to 1:1 with respect to (R,S)-THP (I).

10. A process according to claim 1 wherein the separated diastereoisomer is further purified through one or more crystallizations of the compound itself before recovering (R)-THP (Ia).

11. A process according to claim 1 further comprising the salification of (R)-THP (Ia) or (S)-THP (Ib).

12. The compound (R)-THP.(S)-naproxen or (S)-TH.(S)-naproxen.

13. A process for the preparation of cis-atracurium comprising:
reacting the (R)-THP obtained by the process of claim 1 with 1,5-pentamethylene diacrylate; and
isolating the product from the reacting step.

14. A process according to claim 1 wherein the optically active acid is (R)-mandelic acid.

15. A process according to claim 5 wherein the aqueous hydrogen halide is selected from the group consisting of hydrochloric acid, sulphuric acid and phosphoric acid.

16. A process according to claim 9 wherein the optically active arylpropionic acid is used in a ratio of equivalents of from 0.35:1 to 0.8:1 with respect to (R,S)-THP (I).

17. A process according to claim 9 wherein the optically active arylpropionic acid is used in a ratio of equivalents of from 0.40:1 to 0.65:1 with respect to (R,S)-THP (I).

18. The process of claim 11, wherein the salification of (R)-THP (Ia) or (S) THP (Ib) occurs as the hydrochloride.

19. A process according to claim 1 wherein the optically active acid is selected from the group consisting of (R)-mandelic acid, (S)-O-acetylmandelic acid, L-phenyl lactic acid, (R)- and (S)-methoxyphenylacetic acid, (S)-phenylpropionic acid, and (R)- and (S)-tropic acid.

\* \* \* \* \*

UNITED STATES PATENT AND TRADEMARK OFFICE
CERTIFICATE OF CORRECTION

PATENT NO. : 8,703,955 B2  Page 1 of 1
APPLICATION NO. : 12/808255
DATED : April 22, 2014
INVENTOR(S) : Segnalini et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 281 days.

Signed and Sealed this

Twenty-ninth Day of September, 2015

Michelle K. Lee
*Director of the United States Patent and Trademark Office*